United States Patent [19]

Bigham

[11] Patent Number: 5,019,577

[45] Date of Patent: * May 28, 1991

[54] NOVEL COMPOUNDS AND USE

[75] Inventor: Eric C. Bigham, Chapel Hill, N.C.

[73] Assignee: Burroughs Welcome Co., Research Triangle Park, N.C.

[*] Notice: The portion of the term of this patent subsequent to Nov. 14, 2006 has been disclaimed.

[21] Appl. No.: 181,983

[22] Filed: Apr. 15, 1988

[51] Int. Cl.$^5$ .................. A61K 31/505; C07D 239/49
[52] U.S. Cl. .................... 514/272; 514/269; 544/319; 544/321; 260/998.2; 530/331
[58] Field of Search ............... 544/321, 319; 514/272, 514/908, 269; 260/998.2; 530/331

[56] References Cited

U.S. PATENT DOCUMENTS

| 4,369,319 | 1/1983 | DeGraw, Jr. et al. | 514/908 |
|---|---|---|---|
| 4,833,145 | 5/1989 | Taylor et al. | 514/258 |
| 4,871,743 | 10/1989 | Taylor | 514/272 |
| 4,871,746 | 10/1989 | Taylor et al. | 514/30.3 |
| 4,880,812 | 11/1989 | Kelley | 514/272 |

FOREIGN PATENT DOCUMENTS 239362 9/1987 European Pat. Off. .
268377 5/1988 European Pat. Off. .

OTHER PUBLICATIONS

Journal of Medicinal Chemistry, vol. 6, No. 6, Nov. 1963, pp. 663–669.
Journal of Pharmaceutical Sciences, vol. 52, No. 9, Sep. 1963, p. 819.
B. R. Baker, et al., Analogs of Tetrahydrofolic Acid VII, vol. 52, No. 9, Sep. 1963, pp. 840–843.
Abstract-p. 4797, 28-Heterocyclic Compounds, vol. 68, 1968.
Baker et al., J. of Pharm. Sci., vol. 52, No. 9, 1963, pp. 840–843.
Berezovskij et al., Khim. Farm. Z. H., vol. 1, No. 6 (1967) pp. 5–9.
Koehler et al., JACS, vol. 80, pp. 5778–5786 (1958) "Potential Anticancer Agents, IX, Tetrahydroquinazoline ——".

*Primary Examiner*—Cecilia Shen
*Attorney, Agent, or Firm*—Donald Brown; Lawrence A. Nielsen; Hannah O. Green

[57] ABSTRACT

The present invention provides a compound selected from:

N-[4-(3 -(2,4-diamino-1,6-dihydro-6-oxo-5-pyrimidinyl)propylamino)-2-flurobenzoyl]-(L)-glutamic acid, N-[4-( 3-(2,4-diamino-1,6-dihydro-6-oxo-5-pyrimidinyl)propylamino)-3-flurobenzoyl]-(L)-glutamic acid, N-[4 -(3 -(2,4-diamino-1,6-dihydro-6-oxo-5-pyrimidinyl)propylamino)-3-methylbenzoyl]-(L)-glutamic acid, N-[4-( 2,4-diamino-1,6-dihydro-6-oxo-5-pyrimidinyl)-propylamino)-3-(methoxy)benzoyl](L)-glutamic acid and N-[4-(3 -(2,4-diamino-1,6-dihydro-6-oxo-5-pyrimidinyl)propylamino)-2-chlorobenzoyl](L)-glutamic acid, or a salt thereof, methods for the preparation of the compounds, intermediates in their preparations, pharmaceutical formulations containing them, and their use in the treatment of tumors.

4 Claims, No Drawings

NOVEL COMPOUNDS AND USE

The present invention relates to a group of novel glutamic acids, acid esters and salts, processes and intermediates for their preparation, pharmaceutical formulations containing them, and to their use in medicine and agriculture.

A structurally distinct group of novel substituted glutamic acids and acid esters had now been discovered in which the glutamic acid or acid ester is substituted by a pyrimidylalkylaminobenzoyl chain characterized in that the pyrimidyl moiety is 2,4-diamino-1,6-dihydro-6-oxo-5-pyrimidinyl. They have, moreover, been found to possess anti-neoplastic activity in that the compounds are able to inhibit the unregulated multiplication and proliferation of undifferentiated cells. Such activity has bee demonstrated against human breast adenocarcinoma cells in the cell culture cytotoxicity test which is described hereinafter.

Accordingly, the present invention provides a compound selected from:

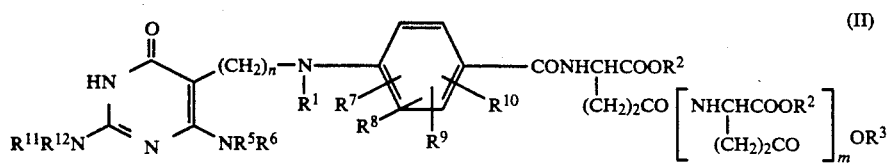

N-[4-(3-(2,4-diamino-1,6-dihydro-6-oxo-5-pyrimidinyl)-propylamino)-2-fluorobenzoyl]-(L)-glutamic acid, N-[4-(3-(2,4-diamino-1,6-dihydro-6-oxo-5-pyrimidinyl)-propylamino)-3-fluorobenzoyl]-(L)-glutamic acid, N-[4-(3-(2,4-diamino-1,6-dihydro-6-oxo-5-pyrimidinyl)-propylamino)-3-methylbenzoyl]-(L)-glutamic acid, N-[4-(3-(2,4-diamino-1,6-dihydro-6-oxo-5-pyrimidinyl)-propylamino)-3-(methoxy)benzoyl]-(L)-glutamic acid and N-[4-(3-(2,4-diamino-1,6-dihydro-6-oxo-5-pyrimidinyl)-propylamino)-2-chlorobenzoyl]-(L)-glutamic acid, or a pharmaceutically acceptable salt thereof, and a pharmaceutically acceptable carrier therefor.

The compounds of the present invention have an asymmetric carbon atom and are, therefore, capable of existing as optical isomers (enantiomers).

Although all such isomers, individually and as mixtures, are included within the scope of the present invention, the L-optical isomers are preferred.

Of the compounds exemplified hereinafter, those that are preferred include the compound of Example 2.

As salts of the compounds of the present invention, there are included acid addition salts derived from either of the two terminal amino groups that substituted the pyrimidyl moiety or from the amino group present in the chain between the phenylene and the -(CH$_2$)$_3$- moiety and salts comprising an anionic species derived from a compound of the invention and a cation. In both types of salts, the anti-neoplastic activity resides in the moiety derived from the compound of the invention as defined herein and the identity of the other component is of less importance although for therapeutic and prophylactic purposes it is, preferably, pharmaceutically acceptable to the patient. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycollic, gluconic, succinic and arylsulphonic, for example p-toluenesulphonic, acids. Examples of salts comprising an anionic species derived from a compound of the invention and a cation include ammonium salts, alkali metal salts, such as sodium and potassium salts, alkaline earth salts, such as magnesium and calcium salts, and salts formed with organic bases, for example, amino salts derived from mono-, di- or tri-(lower alkyl) or (lower alkanol)amines, such as triethanolamine and diethylaminoethylamine, and salts with heterocyclic amines such as piperidine, pyridine, piperazine and morpholine. The pharmaceutically acceptable salts together with the salts which are not thus acceptable have utility in the isolation and/or the purification of the compounds of the invention, and the pharmaceutically unacceptable salts are also useful in being convertible to the pharmaceutically acceptable salts by techniques well known in the art.

The present invention also provides a process for the preparation of a compound of the invention, as defined herein, or a salt thereof, which comprises deacylating a compound of formula (II):

wherein R$^1$, R$^2$, and R$^3$ are hydrogen; one of R$^7$, R$^8$, R$^9$ and R$^{10}$ is chloro, fluoro, methyl or methoxy and the rest are hydrogen; n is 3; m is 0; one of the groups R$^5$, R$^6$, R$^{11}$ and R$^{12}$ is C$_{1-12}$ acyl and the other groups R$^5$, R$^6$, R$^{11}$ and R$^{12}$ are the same or different and are hydrogen or C$_{1-12}$ acyl, and optionally forming a salt.

Preferably, R$^5$, R$^6$, R$^{11}$ and R$^{12}$, when C$_{1-12}$ acyl, are carboxylic C$_{1-12}$ acyl. Most preferably, R$^5$, R$^6$, R$^{11}$ and R$^{12}$, when C$_{1-12}$ acyl, are the same or different and are C$_{1-12}$ carboxylic acyl, in particular C$_{1-6}$ alkanoyl, especially acetyl.

The deacylation of a compound of formula (II) may be carried out conventionally. In the preferred case where R$^5$, R$^6$, R$^{11}$ and R$^{12}$, when C$_{1-12}$ acyl, are the same or different and are C$_{1-6}$ alkanoyl, the deacylation is, preferably, carried out at an elevated temperature in an alcoholic solvent, such as ethanol or ethanol containing a small amount of 2-mercaptoethanol so as to prevent any oxidation of the resulting compound of the invention, in the presence of a base, such as sodium hydroxide.

The optional formation of a salt of a compound of the invention may be carried out conventionally.

The compounds of formula (II) may be prepared by reducing a mixture of a compound of formula (III):

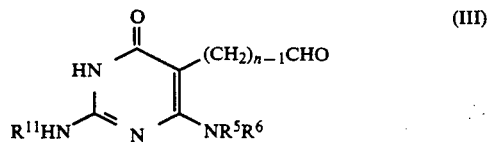

wherein R$^5$, R$^6$, R$^{11}$ and n are as defined herein, and a compound of formula (VI):

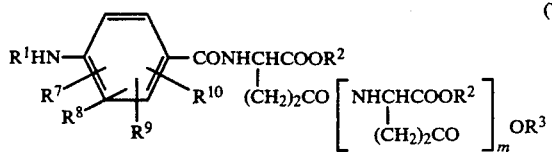

wherein $R^1$, $R^2$, $R^3$, $R^7$, $R^8$, $R^9$ and $R^{10}$ are as defined herein.

The reduction of a mixture of the compounds of formulae (III) and (VI) may be carried out in accordance with conventional reductive alkylation reactions. It is, however, preferred that the reduction is effected with sodium cyanoborohydride in a solvent in the presence of an acid, such as acetic acid which may also function as the solvent.

The compounds of formula (II), wherein n is 3, may also, although less preferably, be prepared by reducing a mixture of a compound of formula (IV):

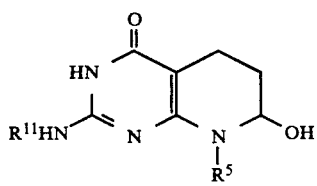

wherein $R^5$ and $R^{11}$ are as defined herein, and a compound of formula (VI) as defined herein.

The reduction of a mixture of the compounds or formulae (IV) and (VI) may be carried out analogously to the reduction of a mixture of the compounds of formulae (III) and (VI) in which sodium cyanoborohydride is used in the presence of an acid, such as acetic acid, to effect the reduction. It is, however, preferred, in the reduction of the mixture of the compounds of formulae (VI) and (IV), that acetic acid is not used also as the solvent but that, for example, methanol or a mixture of methanol and 2-methoxyethanol is used in this regard. It is also preferred that the reduction is carried out in the presence of a dehydrating agent, such as molecular sieves.

The compounds of formulae (III) and (IV) may both be prepared by hydrolysis of a compound of formula (V):

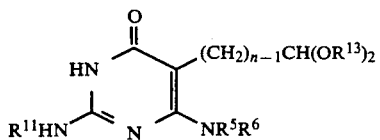

wherein $R^{11}$, $R^5$, $R^6$ and n are as defined herein and $R^{13}$ is $C_{1-4}$ alkyl, such as ethyl.

In the case of the preparation of a compound of formula (III), the hydrolysis may be carried out in a solvent, such as dichloromethane or acetone, in the presence of an acid, such as oxalic acid or 4-toluenesulphonic acid. In addition, in the case of the preparation of a compound of formula (III), wherein n is 3, the hydrolysis may also be carried out simply in water at room or a slightly elevated temperature.

In the case of the preparation of a compound of formula (IV), the hydrolysis is carried out with a compound of formula (V), wherein n is 3, and may be achieved simply in boiling or nearly boiling water.

The compound of formula (V) may be prepared by acylating a compound of formula (VII):

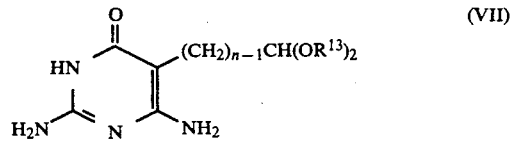

wherein $R^{13}$ and n are as defined herein.

The acylation of a compound of formula (VII) may be carried out conventionally using, for example, an acid anhydride in the presence of a base, such as pyridine.

The compound of formula (VII) may be prepared by reacting a compound of formula (VIII):

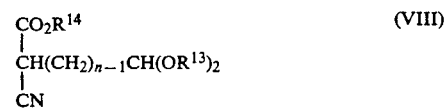

wherein $R^{13}$ and n are as defined herein and $R^{14}$ is $C_{1-4}$ alkyl, such as ethyl, and guanidine.

The reaction between the compound of formula (VIII) and guanidine may be carried out conventionally, for example, in a solvent, such as ethanol, in the presence of a base, such as sodium methoxide, at an elevated temperature.

The compound of formula (VIII) may be prepared by reacting a compound of formula (IX):

wherein $R^{14}$ is as defined herein, and a compound of formula (X):

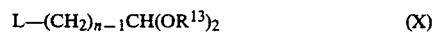

wherein $R^{13}$ and n are as defined herein and L is a leaving group, such as chloro, bromo, iodo or tosyloxy.

The reaction between the compounds of formulae (IX) and (X) may be carried out conventionally, for example, in a solvent, such as ethanol, in the presence of a base, such as sodium methoxide.

The compounds of formulae (VI), (IX) and (X) are commercially available, or may be obtained by carrying out a published process for their preparation, or by carrying out a process analogous to a published process for the preparation of structurally analogous compounds. For example, the compounds of formula (VI) may be obtained by using the process described in J. Am. Chem. Soc., 1958, 80, page 5778 et seq.

While it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as hereinbefore defined, and a pharmaceutically acceptable carrier therefor.

The pharmaceutical formulation may optionally contain other therapeutic agents that may usefully be employed in conjunction with the compound or salt of the present invention, for example a dihydrofolate reductase inhibitor that is capable of enhancing the antineoplastic activity of the compounds and salts of the present invention. The expression "pharmaceutically acceptable" as used herein in relation to the carrier is used in the sense of being compatible with the compound or salt of the invention employed in the formulation and with any other therapeutic agent that may be present, and not being detrimental to the recipient thereof. The carrier itself may constitute one or more excipients conventionally used in the art of pharmacy that enable the compound or salt of the present invention and any other therapeutic agent that may be present, to be formulated as a pharmaceutical formulation.

The pharmaceutical formulations of the present invention include those suitable for oral, parenteral (including subcutaneous, intradermal, intramuscular and intravenous) and rectal administration although the most suitable route will probably depend upon, for example, the condition and identity of the recipient. The formulations may conveniently be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or a non-aqueous liquid such as a syrup, elixir or a draught, or as an oil-in-water liquid emulsion or a water-in-oil liquid emulsion. The formulation may also be a bolus, electuary or paste.

Generally, a tablet is the most convenient pharmaceutical formulation suitable for oral administration. A table may be made by compressing or moulding the active ingredient with the pharmaceutically acceptable carrier. Compressed tablets may be prepared by compressing in a suitable machine the active ingredient in a free-flowing form, such as a powder or granules, in admixture with for example, a binding agent, an inert diluent, a lubricating agent, a disintegrating agent and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions which may contain, for example, an anti-oxidant, a buffer, a bacteriostat and a solution which renders the composition isotonic with the blood of the recipient, and aqueous and non-aqueous sterile suspensions which may contain, for example, a suspending agent and a thickening agent. The formulations may be presented in unit-dose of multi-dose containers, for example sealed ampoules and vials, and may be stored in a freeze-dried (lyophilized) condition requiring only the addition of the sterile liquid carrier, for example water for injection, immediately prior to use.

Extemporaneous injection solutions and suspensions may be prepared from sterile powders, granules and tablets of the kind previously described.

The pharmaceutical formulations of the present invention suitable for rectal administration may be presented as a suppository containing, for example, cocoa butter and polyethylene glycol.

As mentioned hereinbefore, the compounds of the invention have anti-neoplastic activity as demonstrated hereinafter in the human breast adenocarcinoma cell culture cytotoxicity test, in which a representative number of the compounds of the present invention is shown to be active against particular cell lines. It has thus been established that the compounds of the present invention are able to inhibit neoplastic growth. Therefore, the compounds and salts of the present invention are of use in medicine and in particular in the treatment of neoplastic growth, especially lymphocytic leukemia and malignant solid tumors such as melanoma in mammals. Accordingly, the present invention yet further provides a method for the treatment of susceptible malignant tumors and leukemia in an animal, e.g., a mammal, which comprises administering to the animal a therapeutically effective amount of a compound or salt of the present invention. In the alternative, there is also provided a compound or salt of the present invention for use in medicine and in particular for use in the treatment of a neoplastic growth, e.g., leukemia and malignant tumors.

The animal requiring treatment with a compound or salt of the present invention is usually a mammal, such as a human being.

Particular examples of a neoplastic growth requiring treatment include lymphocytic leukemia and malignant tumors.

As mentioned hereinbefore, the antineoplastic activity of the compounds and salts of the present invention may be enhanced by a dihydrofolate reductase inhibitor, for example, 2,4-diamino-6-(2,5-dimethoxybenzyl)-5-methylpyrido[2,3-d]pyrimidine hydrochloride. Therefore, it may be advantageous to employ with the compounds and salts of the present invention a dihydrofolate reductase inhibitor in the treatment of neoplastic growth.

The route by which the compound or salt of the present invention is administered to the animal may be oral, parenteral (including subcutaneous, intradermal, intramuscular, intravenous or rectal). If the compound or salt is presented in the form of a pharmaceutical formulation, which, as mentioned hereinbefore, is preferred, then the actual formulation employed will of course depend on the route of administration elected by the physician or veterinarian. For example, if oral administration is preferred, then the pharmaceutical formulation employed is, preferably, one which is suitable for such a route.

A therapeutically effective amount of a compound or salt of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, in particular lymphocytic leukemia or a malignant tumor, will generally be in the range of 0.5 to 600 mg/kg body weight of recipient (mammal) per day and more usually in the range of 7.0 to 200 mg/kg body weight per day. Thus, for a 70 kg adult mammal, the actual amount per day would usually be from 490 to 14,000 mg and this amount may be given in a single dose per day or more usually in a number (such as two, three, four, five or six) of sub-doses per day such that the total daily dose is the same. An effective amount of a salt of the present invention may be determined as a proportion of the effective amount of the compound per se.

The treatment of neoplastic growth with a compound of the present invention may at times require the administration to the animal of an antidote or rescue agent. Particular examples of such agents include leucovorin, hypoxanthine and 5-aminoimidazole-4-carboxamide ribonucleotide (AICAR), although leucovorin is the most preferred.

The compounds of the invention are active against the mycoplasma, *Spiroplasma citri*. These compounds are, therefore, useful in the treatment or prophylaxis of citrus plants that are infected with this microorganisms. The compounds may be applied to the plants by methods known in the art, such as spraying, dusting, incorporating into the soil or injecting into the plant. The compounds of the invention are also active against certain bacterial organisms that are unable to synthesize their own folic acid and that, therefore, require preformed folate. These organisms are *Lactobacillus casei* and *Streptococcus faecium*.

The following examples and biological data are provided in illustration of the present invention and should not be construed as in any way constituting a limitation thereof.

EXAMPLE 1

Intermediates (a) Preparation of ethyl 2-cyano-5,5-diethoxypentanoate

To a stirred solution of 16.2 (0.30 mol) of sodium methoxide in 100 ml of absolute ethanol was added 160 ml) (170 g, 1.50 mol) of ethyl cyanoacetate. The solution was spin evaporated in vacuo at 40° C. and the residual white solid was dissolved in 200 ml of dry dimethylformamide. To this solution was added 50 ml (50 g, 0.30 mol) of 3-chloropropionaldehyde diethyl acetal and a crystal of sodium iodide, and the solution was heated on a steam bath with magnetic stirring and protection from moisture for 5 hours. The red-brown solution was cooled, poured into 300 ml of ice water and extracted with diethylether (6×200 ml). The organic phase was washed with water (3×50 ml), brine (50 ml) and dried over magnesium suphate. The solution was filtered, spin evaporated in vacuo, and the residue was distilled to give 41.3 g (57%) of a clear liquid, bp 90°-108° (0.05 mm Hg) which was sufficiently pure for the next step. Fractional distillation gave as a main fraction a clear liquid, bp 103°-108° (0.025 mm Hg); NMR (CDCl$_3$) δ 1.20 (t, 6H, CH(OCH$_2$CH$_3$)$_2$), 1.31 (t, 3H, CO$_2$CH$_2$CH$_3$), 1.90 (m, 2H, CH$_2$CHCN), 3.60 (m, 5H, CH(OCH$_2$CH$_3$)$_2$+CHCN), 4.24 (q, 2H, CO$_2$CH$_2$), 4.51 (t, 1H, CH(OCH$_2$)CH$_3$); IR (film) 2265, 1750, 1450 cm$^{-1}$.

(b) Preparation of 3-(2,4-diamino-1,6-dihydro-6-oxo-5-pyrimidinyl)propionaldehyde diethyl acetal To a solution of 22.0 g (407 mmol) of sodium methoxide in 400 ml of absolute ethanol was added 18.2 g (191 mmol) of guanidine hydrochloride and 46.0 g (189 mmol) of ethyl 2-cyano-5,5-diethoxypentanoate. The mixture was refluxed with stirring for 2.5 hours, stirred at ambient temperature overnight and then neutralized with 15 ml of acetic acid. The salts were removed by filtration and washed with 100 ml of ethanol. The combined filtrate and wash were spin evaporated in vacuo to give an off-white solid which was digested with ethyl acetate and cooled. The solid was collected and washed with ethyl acetate. This material, which contained sodium acetate, was dissolved in 150 ml of 1N sodium hydroxide and then acidified with stirring to pH 5–6 with 10 ml of acetic acid. The resultant precipitate was collected, washed with 50 ml of cold water (product partly soluble in water) and dried; yield, 29.07 g (60%), mp 178°–181°.

Recrystallization of a portion from ethyl acetate-ethanol gave the analytical sample, mp 177°-178°; TLC (C$_6$H$_6$:EtOH/5:1); NMR (DMSO-d$_6$) δ 1.11 (t, 6H, CH$_3$), 1.56 (m, 2H, CH$_2$CH$_2$CH), 2.19 (t, 2H, CH$_2$CH$_2$CH), 3.2-3.7 (m, 4H, 2×OCH$_2$), 4.45 (t, 1H, H), (s, H, NH$_2$, 5.98 (s, 2H, NH$_2$), 9.84 (s, 1H, HNC(O)).

Elemental analysis: Calculated for C$_{11}$H$_{20}$N$_4$O$_3$: C, 51.6; H, 7.87; N, 21.9. Found: C, 51.7; H, 7.79; N, 21.7

(c) Preparation of 3-(2-acetylamino-4-diacetylamino-1,6-dihydro-6-oxo-5-pyrimidinyl)propionaldehyde diethyl acetal A stirred mixture of 7.20 g (28.1 mmol) of 3-(2,4-diamino-1,6-dihydro-6-oxo-5-pyrimidinyl)propionaldehyde diethyl acetal, 30 ml of dry pyridine and 30 ml of freshly distilled acetic anhydride was heated on an oil bath at 90° for 6 hours and then stirred at ambient temperature overnight. Solution occurred within 15 minutes as a mixture of diacetyl and triacetyl pyrimidinone formed; extended reaction was required to obtain only the title compound. The solution was spin evaporated in vacuo to give an oil. Ethyl acetate was added and spin evaporated several times until a solid was obtained. The solid was dispersed in cyclohexane and collected; yield, 8.88 g (82%), mp 126°-137° (one spot on TLC). Recrystallization of a portion from cyclohexane-ethylacetate gave the analytical sample, mp 138°-139°; TLC (C$_6$H$_6$:EtOH/5:1); NMR (DMSO-d$_6$) δ 1.08 (t, 6H, 2CH$_2$CH$_3$), 1.63 (m, 2H, CH$_2$CH$_2$CH), 2.13 (s, 3H, Ac), 2.27 (s, 6H, 2Ac), 2.2 (2H, CH$_2$CH$_2$CH, superimposed on the acetyl singlets), 3.2-3.7 (m, 4H, 2×OCH$_2$), 4.42 (t, 1H, CH), 11.87 (br s, 2H, AcNH and HNC(O)).

Elemental analysis: Calculated for C$_{17}$H$_{26}$N$_4$O$_6$: C, 53.4; H, 6.85; N, 14.6. Found: C, 53.7; H, 6.87; N, 14.6.

Route Via Compound of Formula (III):

(d) Preparation of 3-(2-Acetylamino-4-diacetylamino-1,6-dihydro-6-oxo-5-pyrimidinyl)propionaldehyde Method 1: A solution of 3-(2-acetylamino-4-diacetylamino-1,6-dihydro-6-oxo-5-pyrimidinyl)propionaldehyde diethyl acetal (1.00 g, 2.6 mmol) in distilled water (30 ml) was stirred at room temperature for 18 hours. This solution was extracted with ethyl ether (3×50 ml), and chloroform (5×50 ml). The chloroform extracts were combined, washed with water (25 ml), brine (25 ml), dried (MgSO$_4$) and spin evaporated in vacuo. The residue was recrystallized from chloroform/cyclohexane to yield 0.200 g (25% of theory) of analytically pure 3-(2-acetylamino-4-diacetylamino-1,6-dihydro-6-oxo-5-pyrimidinyl)propionaldehyde quarter hydrate, mp 164°–168° C.

Elemental analysis: Calc for C$_{13}$H$_{16}$N$_4$O$_5$ ¼ H$_2$O (MW 312.803): C, 49.9; H, 5.32; N, 17.9. Found: C, 49.8; H, 5.30; N, 17.6.

Method 2: A solution of 3-(2-acetylamino-4-diacetylamino-1,6-dihydro-6-oxo-5-pyrimidinyl)propionaldehyde diethyl acetal (30.0 g, 78.5 mmol) in distilled water (600 ml) was stirred at 53° C. for 3.5 hours and spin evaporated in vacuo at 45° C. The residue was dissolved in dichloromethane (750 ml), washed with brine (50 ml), dried (MgSO$_4$), and spin evaporated in vacuo to a dry solid.

Recrystallization from acetone gave 16.23 g (67% of theory) of 3-(2-acetylamino-4-diacetylamino-1,6-dihydro-6-oxo-5-pyrimidinyl)propionaldehyde, mp 164°–168° C., which was identical to that prepared by Method 1.

EXAMPLE 2

Preparation of
N-[4-(3-(2,4-Diamino-1,6-dihydro-6-oxo-5-pyrimidinyl)propylamino)-2-fluorobenzoyl]-(L)-glutamate (a) Preparation of di-tert-butyl
N-(4-nitro-2-fluorobenzoyl)-(L)-glutamate A solution of 2-fluoro-4-nitrobenzoic acid (6.26 g, 33.8 mmoles), (L)-glutamate di-tert-butyl ester hydrochloride (10.0 g, 33.8 mmoles), and 1-hydroxybenzotriazole (4.57 g, 33.8 mmoles) in dry dimethylformamide (150 mL) was stirred under nitrogen while triethylamine (3.42 g, 4.71 mL, 33.8 mmoles) was added in one portion. After 15 minutes, 1.3-dicyclohexylcarbodiimide (7.67 g, 37.2 mmoles) was added in portions during 1 minute. The reaction mixture was filtered after 20 hours and the solids rinsed with dichloromethane (1×50 mL). The filtrate was spin evaporated to an amber residue that was partitioned between dichloromethane and saturated bicarbonate solution (200 mL each). The organic phase was washed successively with saturated bicarbonate, 5% citric acid, and brine (1×200 mL each). The organic phase was then dried (MgSO$_4$), filtered, spin evaporated, and dried (high vacuum) to an oily yellow solid (11.9 g, 83%) that showed a major spot on tlc (silica, 2:1 hexane/ethyl acetate, R$_f$=0.5). The product was purified by the flash chromatography technique to give a light green gum; yield, 9.7 g (67%); $^1$H-NMR (CDCl$_3$) δ 1.42 (s, 9H), 1.50 (s, 9H), 2.02–2.41 (m, 4H), 4.72 (m, 1H), 7.44 (br t, 1H), 8.0–8.3 (m, 3H); uv (MeOH) 260 nm max (11000), 225 min (4710), 215 sh (7680); mass spec (CI) m/e 427 (24%), 371 (20), 315 (100).

Anal. Calcd. for C$_{20}$H$_{27}$FN$_2$O$_7$ (M$_r$ 426.44): C, 56.33; H, 6.38; N, 6.57. Found: C, 56.39; H, 6.40; N, 6.57.

(b) Preparation of Di-tert-butyl
N-(4-amino-2-fluorobenzoyl)-(L)-glutamate

A solution of di-tert-butyl-N (4-nitro-2-fluorobenzoyl)-(L)-glutamate (3.6 g, 8.4 mmoles) in 95% ethanol (100 mL) was mixed with 10% palladium on carbon (0.25 g) and placed on a Parr apparatus. The mixture was shaken under hydrogen atmosphere for 2 hours. The reaction mixture was filtered, spin evaporated, and dried to give a white solid, di-tert-butyl N-(4-amino-2-fluorobenzoyl)-(L)-glutamate yield, 3.0 g (91%); mp 91°–95° C.; $^1$H-NMR (CDCl$_3$) δ 1.41 (s, 9H), 1.48 (s, 9H), 2.0–2.4 (m, 4H), 2.8 (br s, 2H), 4.71 (m, 1H), 6.34 (d, 1H), 6.48 (d, 1H), 7.17 (q, 1H), 7.86 (t, 1H); uv (MeOH) 280 nm max (16800), 238 min (2760), 212 sh (12100); mass spec (CI) m/e 397 (21%), 341 (13), 285 (100).

Anal. Calcd. for C$_{20}$H$_{29}$FN$_2$O$_5$ (M$_r$ 396.45): C, 60.59; H, 7.37; N, 7.07. Found: C, 60.33; H, 7.47; N, 6.99.

(c) Preparation of Di-tert-butyl
N-(4-((3-(2-(Acetylamino)-4-(diacetylamino-1,6-dihydro-6-oxo-5-pyrimidinyl)propyl)amino)-2-fluorobenzoyl)-(L)-glutamate Both di-tert-butyl N-(4-amino-2-fluorobenzoyl)-(L)-glutamate (1.29 g, 3.24 mmoles) and 3-(2-acetylamino-4-diacetylamino-1,6-dihydro-6-oxo-5-pyrimidinyl)propionaldehyde (1.00 g, 3.24 mmoles) were stirred in absolute ethanol (25 mL) under nitrogen while glacial acetic acid (1.5 mL) was added dropwise during 1 minute. After solution was achieved (1 hour), activated 3 Å molecular sieves (5 mL) were added. After stirring 5 hours, sodium cyanoborohydride (0.20 g, 3.24 mmoles) was added in one portion. The reaction mixture was filtered after 18 hours and the solids were rinsed with ethanol (2×10 mL). The filtrate was spin evaporated to a brown residue that was partitioned between ethyl acetate and water (50 mL each). The organic phase was washed (1×100 mL 1:1 water/brine), dried (MgSO$_4$), and filtered to give a clear brown solution that showed a major spot on tlc (silica, 5% methanol/ethyl acetate, R$_f$=0.5). The solution was spin evaporated onto silica gel (20 g) and the product eluted by the flash chromatography technique to give a white solid; yield, 1.28 g (57%); mp >120° C. (grad. dec.); $^1$H-NMR (DMSO-d$_6$) δ 1.36 and 1.39 (2s, 18H), 1.62 (m, 2H), 1.8–2.4 (m, 6H), 2.09 (s, 3H), 2.19 (s, 6H), 2.98 (m, 2H), 4.31 (m, 1H), 6.25 (d, J$_o^{F,H}$=15 Hz, 1H), 6.38 (d, J$_o^{H,H}$=9 Hz, 1H), 6.66 (br m, 1H), 7.44 (t, J$_o^{H,H}$ and J$_m^{F,H}$=9 Hz, 1H), 7.68 (t, 1H), 11–12 (v br s, 1H); uv (MeOH) 299 nm max (11900), 258 min (3250); mass spec (FAB) m/e 689 (25%), 430 (100), 388 (56), 277 (40).

Anal. Calcd. for C$_{33}$H$_{45}$FN$_6$O$_9$.H$_2$O (M$_r$ 706.77): C, 56.08; H, 6.70; N, 11.89. Found: C, 56.15; H, 6.57; N, 11.59.

(d) Preparation of
N-[4-(3-(2-4-Diamino-1,6-dihydro-6-oxo-5-pyrimidinyl)propylamino)-2-fluorobenzoyl]-(L)-glutamic acid A solution of di-tert-butyl N-(4-((3-(2-(acetylamino)-4-(diacetylamino-1,6-dihydro-6-oxo-5-pyrimidinyl)propyl)amino)-2-fluorobenzoyl)-(L)-glutamate (0.70 g, 1.0 mmol) in freshly distilled trifluoroacetic acid (10 mL) was stirred under nitrogen for 1.5 hours. The solution was spin evaporated and dried (high vacuum) to a light yellow residue that was mixed with 1.0N sodium hydroxide (20 mL) and stirred under nitrogen at 55° C. for 18 hours. The reaction mixture was chilled (ice bath), neutralized by dropwise addition of glacial acetic acid, and then adjusted to pH 2.5 by dropwise addition of 6N hydrochloric acid. After stirring cold for 2 hours, the resulting precipitate was filtered. The wet cake was recrystallised from dimethylformamide/water to give a cream solid; yield, 0.26 g (57%); mp 195°–200° C.; $^1$H-

NMR (DMSO-d$_6$) δ 1.55 (m, 2H), 1.8–2.1 (m, 2H), 2.1–2.3 (m, 4H), 2.98 (m, 2H), 4.36 (m, 1H), 5.75 (br s, 2H), 5.92 (br s, 2H), 6.27 (dxd, $J_o^{F,H}$=15 Hz, $J_m^{H,H}$=2 Hz, 1H), 6.39 (dxd, $J_o^{H,H}$=9 Hz, $J_m^{H,H}$=2 Hz, 1H), 6.56 (br m, 1H), 7.46 (t, $J_o^{H,H}$ and $J_m^{F,H}$=9 Hz, 1H), 7.68 (t, 1H), 9.8 (v br s, 1H), 12.4 (v br s, 2H); uv (0.1N NaOH) 295 nm max (21400), 288 min (20900), 274 max (24400), 244 min (8230), 220 max (20400).

Anal. Calcd. for C$_{19}$H$_{23}$FN$_6$O$_6$·0.7H$_2$O·0.3C$_3$H$_7$NO (M$_r$484.96): C, 49.29; H, 5.51; N, 18.20. Found: C, 49.24; H, 5.38; N, 18.09.

EXAMPLE 3

Preparation of
N-[4-(3-(2,4-Diamino-1,6-dihydro-6-oxo-5-pyrimidinyl)propylamino)-3-fluorobenzoyl]-(L)-glutamic acid

(a) Preparation of Diethyl N-(4-nitro-3-fluorobenzoyl)-(L)-glutamate

A solution of 3-fluoro-4-nitrobenzoic acid (6.00 g, 32.4 mmoles), (L)-glutamic acid diethyl ester hydrochloride (7.77 g, 32.4 mmoles), and 1-hydroxybenzotriazole (4.38 g, 32.4 mmoles) in dry dimethylformamide (150 mL) was stirred under nitrogen while triethylamine (4.52 mL, 3.28 g, 32.4 mmoles) was added dropwise during 1 minute. To the reaction mixture was added 1,3-dicyclohexylcarbodiimide (7.36 g, 35.7 mmoles) in portions during 1 minute. After 20 hours the reaction mixture was filtered and the solids rinsed with dichloromethane (1×50 mL). The filtrate was spin evaporated (high vacuum) to an amber residue that was partitioned between dichloromethane and saturated bicarbonate solution (200 mL each). The organic phase was washed with saturated bicarbonate solution, 5% citric acid, and brine (1×200 mL each, respectively). The organic phase was then dried (MgSO$_4$), filtered, spin evaporated, and dried (high vacuum) to give a yellow solid (7.6 g, 63%) that showed a major spot on tlc (silica, 2:1 hexane/ethyl acetate, Rf=0.3). The product was purified by the flash chromatography technique (same solvent system) to give a light yellow solid; yield, 5.7 g (48%); mp 78°–80° C.; $^1$H-NMR (CDCl$_3$) δ 1.25 and 1.31 (2t overlapped, 6H), 2.2–2.3 (m, 2H), 2.5–2.6 (m, 2H), 4.14 and 4.25 (2q overlapped, 4H), 4.71 (m, 1H), 7.58 (br d, 1H), 7.7–8.2 (m, 3H); uv (MeOH) 253 nm max (8000), 232 min (5890); mass spec (CI) m/e 371 (100%), 325·(33).

Anal. Calcd. for C$_{16}$H$_{19}$FN$_2$O$_7$ (M$_r$ 370.33): C, 51.89; H, 5.17; N, 7.56. Found: C, 51.98; H, 5.20; N, 7.55.

(b) Preparation of Diethyl N-(4-amino-3-fluorobenzoyl)-(L)-glutamate

A solution of diethyl N-(4-nitro-3-fluorobenzoyl)-(L)-glutamate (5.3 g, 14 mmoles) in 95% ethanol (150 mL) was mixed with 10% palladium on carbon (0.4 g) and placed on a Parr apparatus. The mixture was shaken under hydrogen atmosphere for 1.5 hours. The reaction mixture was filtered, spin evaporated, and dried to give a cream solid; yield, 4.7 g (98%); mp 92°–97° C.; $^1$H-NMR (CDCl$_3$) δ 1.22 and 1.29 (2t overlapped, 6H), 1.6 (br s, 2H), 2.1–2.5 (m, 4H), 4.10 and 4.22 (2q overlapped, 4H), 4.74 (m, 1H), 6.75 (t, 1H), 6.84 (d, 1H), 7.4–7.5 (m, 2H); uv (MeOH) 281 nm max (12000), 236 min (1480), 210 sh (10600); mass spec (CI) m/e 341 (100%), 138 (64).

Anal. Calcd. for C$_{16}$H$_{21}$FN$_2$O$_5$ (M$_r$ 340.35): C, 56.46; H, 6.22; N, 8.23. Found: C, 56.43; H, 6.27; N, 8.17.

(c) Preparation of Diethyl N-[4-(3-(2-acetylamino-4-diacetylamino-1,6-dihydro-6-oxo-5-pyrimidinyl)propylamino)-3-fluorobenzoyl]-(L)-glutamate Both diethyl N-(4-amino-3-fluorobenzoyl)-(L)-glutamate (2.21 g, 6.49 mmoles) and 3-(2-acetylamino-4-diacetylamino-1,6-dihydro-6-oxo-5-pyrimidinyl)propionaldehyde (2.00 g, 6.49 mmoles) were stirred in absolute ethanol (50 mL) under nitrogen while glacial acetic acid (3mL) was added dropwise during 1 minute. After solution was achieved (1 hour), activated 3 Å molecular sieves (10 mL) were added and stirring was continued 5 hours. The reaction mixture was chilled (ice bath) and sodium cyanoborohydride (408 mg, 6.49 mmoles) added in one portion. After stirring cold 0.5 hour, the bath was removed. The reaction mixture was allowed to warm to ambient temperature and stir 16 hours. The reaction mixture was filtered and the solids rinsed with ethanol (100 mL). The filtrate was spin evaporated to a brown residue that was partitioned between ethyl acetate and water (100 mL each). The organic phase was separated, washed (1×100 mL 1:1 water/brine), dried (MgSO$_4$), filtered, and spin evaporated to a small volume (20 mL). The solution was chromatographed on silica gel (175 g) using an ethyl acetate rinse (450 mL) followed by elution of the product with 5% added methanol. Like fractions were combined by spin evaporation and dried to give a white solid; yield, 2.66 g (65%); mp 76°–84° C. (dec); $^1$H-NMR (DMSO-d$_6$) δ 1.15 and 1.16 (2t overlapped, 6H), 1.64 (m, 2H), 2.00 (m, 2H), 2.11 (s, 3H), 2.20 (s, 6H), 2.27 (m, 2H), 2.40 (t, 2H), 3.10 (m, 2H), 3.9–4.1 (2q overlapped, 4H), 4.35 (m, 1H), 6.10 (m, 1H), 6.66 (t, $J_o^{H,H}$ and $J_m^{F,H}$=9 Hz, 1H), 7.5–7.6 (m, 2H), 8.35 (d, 1H), 11.9 (v br d, 1H); uv (MeOH) 299 nm max (28000), 257 min (7500); mass spec (FAB) m/e 633 (23%), 430 (100), 388 (87).

Anal. Calcd. for C$_{29}$H$_{37}$FN$_6$O$_9$ (M$_r$ 632.64): C, 55.06; H, 5.90; N, 13.28. Found: C, 54.99; H, 5.93; N, 13.22.

(d) Preparation of N-[4-(3-(2,4-Diamino-1,6-dihydro-6-oxo-5-pyrimidinyl)propylamino)-3-fluorobenzoyl]-(L)-glutamic acid A solution of diethyl N-[4-(3-(2-acetylamino-4-diacetylamino-1,6-dihydro-6-oxo-5-pyrimidinyl)-propylamino)-3-fluorobenzoyl]-(L)-glutamate (500 mg, 0.790 mmoles) in 1.0N sodium hydroxide (50 mL) was stirred at 55° C. under nitrogen for 18 hours. After cooling to room temperature, the reaction mixture was adjusted to pH 4.0 by the gradual dropwise addition of glacial acetic acid to precipitate a white solid. The slurry was chilled (ice bath) 1 hour before the solid was filtered, rinsed quickly with ethyl ether (1×15 mL), and dried to give a white solid (376 mg, >100%). A portion (200 mg) was recrystallised from dimethylformamide/water to give the analytical sample as a white solid; yield, 119 mg (60% recovery); mp >175° C. (grad dec); $^1$H-NMR (DMSO-d$_6$) δ 1.56 (m, 2H), 1.8–2.1 (m, 2H), 2.1–2.4 (m, 4H), 3.07 (m, 2H), 4.34 (m, 1H), 5.78 (s, 2H), 5.93 (s, 2H), 6.24 (br s, 1H), 6.70 (t, $J_o^{H,H}$ and $J_m^{F,H}$=9 Hz, 1H), 7.55 and 7.56 (2d overlapped, $J_o^{F,H}$=12 Hz, $J_o^{H,H}$=9 Hz, 2H), 8.23 (d, 1H), 9.8 (v br s, 1H), 12.3 (v br s, 2H); uv (0.1N NaOH) 295 nm max (19800), 287 min (19200), 273 max (23200), 242 min (8120), 220 max (18800).

Anal. Calcd. for $C_{19}H_{23}FN_6O_6 \cdot 0.4H_2O \cdot 0.3C_3H_7NO$ ($M_r$ 479.56): C, 49.84; H, 5.44; N, 18.40. Found: C, 50.04; H, 5.38; N, 18.25.

EXAMPLE 4

Preparation of
N-[4-(3-(2,4-Diamino-1,6-dihydro-6-oxo-5-pyrimidinyl)propylamino)-3-methylbenzoyl]-(L)-glutamic acid (a) Preparation of Diethyl
N-(4-amino-3-methylbenzoyl)-(L)-glutamate A solution of diethyl N-(3-methyl-4-nitrobenzoyl)-(L)-glutamate (Cosulich, D. B. et al., *J. Am. Chem. Soc.*, 1953, 75, 4675) (11.0 g, 30.0 mmoles) in 95% ethanol (250 mL) was mixed with 10% palladium on carbon (0.8 g) and placed on a Parr apparatus. The mixture was shaken under hydrogen atmosphere for 2 hours. The reaction mixture was filtered, spin evaporated, and dried to give a beige solid; yield, 10.1 g (100%); mp 79°-82° C.; $^1$H-NMR (DMSO-d$_6$) δ 1.15 and 1.16 (2t overlapped, 6H), 2.00 (m, 2H), 2.06 (s, 3H), 2.39 (t, 2H), 4.03 and 4.06 (2q overlapped, 4H), 4.33 (m, 1H), 5.40 (s, 2H), 6.56 (d, Jo=8 Hz, 1H), 7.47 (d, Jo=8 Hz, 1H), 7.50 (s, 1H), 8.16 (d, 1H); uv (MeOH) 284 nm max (17000), 241 min (3020); mass spec (CI) m/e 337 (44%), 134 (100).

Anal. Calcd. for $C_{17}H_{24}H_2O_5$ ($M_r$ 336.38): C, 60.70; H, 7.19; N, 8.33. Found: C, 60.76; H, 7.23; N, 8.31.

(b) Preparation of Diethyl
N-[4-(3-(2-acetylamino-4-diacetylamino-1,6-dihydro-6-oxo-5-pyrimidinyl)propylamino)-3-methylbenzoyl]-(L)-glutamate Both diethyl N-(4-amino-3-methylbenzoyl)-(L)-glutamate (2.18 g, 6.49 mmoles) and 3-(2-acetylamino-4-diacetylamino-1,6-dihydro-6-oxo-5-pyrimidinyl)propionaldehyde (2.00 g, 6.49 mmoles) were stirred in absolute ethanol (50 mL) under nitrogen while glacial acetic acid (3 mL) was added dropwise during 1 minute. After solution was achieved (1 hour), activated 3 Å molecular sieves (10 mL) were added and stirring was continued 5 hours. The reaction mixture was chilled (ice bath) and sodium cyanoborohydride (408 mg, 6.49 mmoles) added in one portion. After stirring cold 0.5 hour, the bath was removed and the reaction mixture allowed to warm to ambient temperature. The solids were filtered and rinsed with ethanol (100 mL) after 16 hours. The filtrate was spin evaporated to a residue that was partitioned between ethyl acetate and water (100 mL each). The organic phase was separated, washed (1×100 mL 1:1 water/brine), dried (MgSO$_4$), filtered, and spin evaporated to a small volume (15 mL). The solution was chromatographed on silica gel (175 g) using an ethyl acetate rinse (450 mL) followed by elution of the product with 5% added methanol. Like fractions were combined by spin evaporation and dried to give a clear semi-solid; yield, 1.45 g (36%); $^1$H-NMR (DMSO-d$_6$) δ 1.15 and 1.16 (2t overlapped, 6H), 1.66 (m, 2H), 2.00 (m, 2H), 2.08 (s, 3H), 2.11 (s, 3H), 2.19 (s, 6H), 2.29 (m, 2H), 2.39 (t, 2H), 3.11 (m, 2H), 3.9–4.1 (2q overlapped, 4H), 4.33 (m, 1H), 5.46 (m, 1H), 6.47 (d, Jo=8 Hz, 1H), 7.53 (s, 1H), 7.57 (d, Jo=8 Hz, 1H), 8.20 (d, 1H), 11.8 (v br s, 1H); uv (MeOH) 301 nm max (31000), 258 min (6050); mass spec (FAB) m/e 628 (8%), 426 (100), 384 (95).

Anal. Calcd. for $C_{30}H_{40}N_6O_9 \cdot 0.3 H_2O \cdot 0.5 C_4H_8O_2$ ($M_r$ 678.14): C, 56.68; H, 6.63; N, 12.39. Found: C, 56.61; H, 6.70; N, 12.46.

(c) Preparation of
N-[4-(3-(2,4-Diamino-1,6-dihydro-6-oxo-5-pyrimidinyl)propylamino)-3-methylbenzoyl]-(L)-glutamic acid A solution of diethyl N-[4-(3-(2-acetylamino-4-diacetylamino-1,6-dihydro-6-oxo-5-pyrimidinyl)propylamino)-3-methylbenzoyl]-(L)-glutamate (0.70 g, 1.1 mmoles) in 1.0N sodium hydroxide (20 mL) was stirred at 55° C. under nitrogen for 18 hours. The reaction mixture was chilled (ice bath) and adjusted to pH 2.5 by the gradual dropwise addition of 6.0N hydrochloric acid. After stirring cold 2 hours, the resulting precipitate was filtered. An attempted recrystallization of the wet cake from dimethylformamide/water failed, so the solution was spin evaporated to a clear oil. The oil was mixed with pH 2.1 aqueous HCl (20 mL) and sonicated 5 minutes to obtain a cream solid which was filtered and dried to give the product; yield, 0.12 g (24%); mp 181° C. (eff.); $^1$H-NMR (DMSO-d$_6$) δ 1.58 (m, 2H), 1.8–2.1 (m, 2H), 2.12 (s, 3H), 2.2–2.4 (m, 4H), 3.08 (m, 2H), 4.34 (m, 1H), 5.78 (br s, 2H), 5.94 (br s, 2H), 6.52 (d, Jo=9 Hz, 1H), 7.53 (s overlapped, 1H), 7.57 (d overlapped, Jo=10 Hz, 1H), 8.06 (d, 1H), 10.0 (v br s, 1H), 12.2 (v br s, 2H); uv (0.1N NaOH) 296 nm max (18000), 286 min (17500), 274 max (19900), 247 min (5890), 215 max (21000).

Anal. Calcd. for $C_{20}H_{26}N_6O_6 \cdot H_2O \cdot 0.2C_3H_7NO$ ($M_r$ 479.10): C, 51.64; H, 6.19; N, 18.13. Found: C, 51.63; H, 6.07; N, 18.07.

EXAMPLE 5

Preparation of
N-[4-(3-(2,4-Diamino-1,6-dihydro-6-oxo-5-pyrimidinyl)propylamino)-3-(methoxy)benzoyl]-(L)-glutamic acid (a) Preparation of Diethyl
N-(3-methoxy-4-nitrobenzoyl)-(L)-glutamate A solution of 3-methoxy-4-nitrobenzoic acid (10.0 g, 50.7 mmoles), (L)-glutamate diethyl ester hydrochloride (12.2 g, 50.7 mmoles), and 1-hydroxyenzotriazole (6.85 g, 50.7 mmoles) in dry dimethylformamide (250 mL) was stirred under nitrogen while triethylamine (5.13 g, 7.07 mL, 50.7 mmol) was added dropwise during 1 minute. After 15 minutes, 1,3-dicyclohexylcarbodiimide (11.5 g, 55.8 mmoles) was added in portions during 2 minutes. The reaction mixture was filtered after 18 hours and the solids were rinsed with dichloromethane (2×50 mL). The filtrate was spin evaporated and dried to an amber residue that was dissolved in dichloromethane (300 mL). The organic phase was washed successively with saturated bicarbonate solution, 5% citric acid, and 1:1 brine/water (1×300 mL each). The organic phase was then dried (MgSO$_4$) and filtered to give a brown-orange solution that showed a major spot on tlc (silica, 2:1 hexane/ethyl acetate, R$_f$=0.2). The solution was poured onto a silica gel column (500 g, pre-wet with dichloromethane) and rinsed with dichloromethane (500 mL). The product was removed by gradient elution using 10% and 15% added ethyl acetate (8×250 mL fractions each). Like fractions were combined by spin evaporation and dried (high vacuum) to give a clear yellow oil; yield, 11.5 g (59%); $^1$H-NMR (DMSO-d$_6$) δ 1.15 and 1.18 (2t overlapped, 6H), 1.9–2.2 (m, 2H), 2.45 (t obscured by DMSO, 2H), 3.98 (s, 3H), 3.9–4.2 (2q overlapped, 4H), 4.46 (m, 1H), 7.58 (dxd, J$_o$=8 Hz, J$_m$=2 Hz, 1H), 7.71

(d, $J_m=2$ Hz, 1H), 7.97 (d, $J_o=8$ Hz, 1H), 9.00 (d, 1H); uv (MeOH) 327 nm max (2940), 295 min (2090), 257 sh (6640), 235 sh (9140), 203 max (29700); mass spec (CI) m/e 383 (100%). Anal. Calcd. for $C_{17}H_{22}N_2O_8$ (Mr 382.37): C, 53.40; H, 5.80; N, 7.33. Found: C, b 53.29; H, 5.85; N, 7.29.

(b) Preparation of Diethyl N-(4-amino-3-methoxybenzoyl)-(L)-glutamate

A solution of diethyl N-(3-methoxy-4-nitrobenzoyl)-(L)-glutamate (11.0 g, 28.8 mmoles) in 95% ethanol (200 mL) was mixed with 10% palladium on carbon (0.8 g) and placed on a Parr apparatus. The mixture was shaken under hydrogen atmosphere for 1 hour. The reaction mixture was filtered, spin evaporated, and dried to give a clear viscous oil which on long-standing hardened to a white wax; yield, 9.95 g (99%); $^1$H-NMR (DMSO-d$_6$) δ 1.15 and 1.17 (2t overlapped, 6H), 1.8–2.2 (m, 2H), 2.40 (t, 2H), 3.79 (s, 3H), 4.0–4.2 (2 q overlapped, 4H), 4.36 (m, 1H), 5.29 (br s, 2H), 6.60 (d, $J_o=8$ Hz, 1H), 7.3–7.4 (m, 2H), 8.25 (d, 1H); uv (MeOH) 301 nm max (17800), 280 sh (15700), 266 min (12600), 263 max (13200), 256 sh (12500), 245 min (8630), 204 max (40900); mass spec (CI) m/e 353 (56%), 150 (100).

Anal. Calcd. for $C_{17}H_{24}N_2O_6 \cdot 0.1H_2O \cdot 0.3C_2H_6O$ (Mr 368.01): C, 57.44; H, 7.12; N, 7.61. Found: C, 57.22; H, 6.95; N, 7.83.

(c) Preparation of Diethyl N-[4-(3-(2-acetylamino-4-diacetylamino-1,6-dihydro-6-oxo-5-pyrimidinyl)propylamino)-3-methoxybenzoyl]-(L)-glutamate Both diethyl N-(4-amino-3-methoxybenzoyl)-(L)-glutamate (3.52 g, 9.99 mmoles) and 3-(2-acetylamino-4-diacetylamino-1,6-dihydro-6-oxo-5-pyrimidinyl)propionaldehyde (3.08 g, 9.99 mmoles) were stirred in absolute ethanol (100 mL) under nitrogen while glacial acetic acid (6 mL) was added dropwise during 1 minute. After solution was achieved (0.5 hour), activated 3 Å molecular sieves (20 mL) were added and stirring was continued 2 hours. The reaction mixture was chilled (ice bath) and sodium cyanoborohydride (628 mg, 9.99 mmoles) added in one portion. After stirring cold 0.5 hour, the bath was removed and the reaction mixture allowed to warm to ambient temperature. The reaction mixture was filtered after 16 hours and the solids were rinsed with ethanol (100 mL). The filtrate was spin evaporated and dried to a cream foam that was dissolved in ethyl acetate (100 mL). The organic phase was washed (2×100 mL 1:1 brine/water) and poured onto a silica gel column (175 g, pre-wet with ethyl acetate). The column was rinsed with ethyl acetate (400 mL) and then the product eluted with 5% added methanol. Like fractions were combined by spin evaporation and dried to give a white solid; yield, 2.07 g (32%); mp 73°–84° C. (eff.); 1H-NMR (DMSO-d6) δ 1.15 and 1.17 (2t overlapped, 6H), 1.65 (br m, 2H) 1.9–2.3 (br m, 4H), 2.12 (s, 3H), 2.20 (s, 6H), 2.40 (t, 2H), 3.10 (br m, 2H), 3.80 (s, 3H), 4.0–4.2 (2 q overlapped, 4H), 4.39 (m, 1H), 5.46 (br t, 1H), 6.47 (d, Jo=8 Hz, 1H), 7.29 (d, Jm=2 Hz, 1H), 7.42 (dxd, Jo=8 Hz, Jm=2 hz, 1H), 8.28 (d, 1H), 11.9 (v br s, 2H); uv (MeOH) 306 nm max (25800), 258 min (3940), 227 sh (17800), 205 max (32400), mass spec (FAB) m/e 645.6 (62%), 442.5 (81), 400.1 (100).

Anal. Calcd. for $C_{30}H_{40}N_6O_{10}$ (Mr 644.68): C, 55.89; H, 6.25; N, 13.04. Found: C, 55.73; H, 6.33; N, 12.94.

(d) Preparation of N-[4-(3-(2,4-Diamino-1,6-dihydro-6-oxo-5-pyrimidinyl)propylamino)-3-methoxybenzoyl]-(L)-glutamic acid A solution of diethyl N-[4-(3-(2-acetylamino-4-diacetylamino-1,6-dihydro-6-oxo-5-pyrimidinyl)-propylamino)-3-methoxybenzoyl]-(L)-glutamate (1.00 g, 1.55 mmoles) in 1.0N sodium hydroxide (25 mL) was stirred at 55° C. under nitrogen for 18 hours. The reaction mixture was chilled (ice bath) and adjusted to pH 2.5 by the gradual dropwise addition of 6N hydrochloric acid. After stirring cold 0.5 hour, the resulting precipitate was filtered, rinsed with pH 2.1 aqueous hydrochloric acid (2×25 mL), and dried to give a white solid; yield, 596 mg (83%); mp 165°–184° C. (grad. dec.); $^1$H-NMR (DMSO-d$_6$) δ 1.56 (m, 2H), 1.8–2.2 (br m, 2H), 2.2–2.4 (m, 4H), 3.07 (m, 2H), 3.81 (s, 3H), 4.37 (m, 1H), 5.6 (br s, 1H), 5.74 (s, 2H), 5.93 (s, 2H), 6.49 (d, $J_o=8$ Hz, 1H), 7.29 (d, $J_m=2$ Hz, 1H), 7.41 (dxd, $J_o=8$ Hz, $J_m=2$ Hz, 1H), 8.15 (d, 1H), 9.8 (v br s, 1H), 12.3 (v br s, 2H); uv (0.1N NaOH) 306 nm max (15100), 287 min (11700), 273 max (15200), 250 min (6500), 215 max (25800). Anal. Calcd. for $C_{20}H_{26}N_6O_7 \cdot 0.7H_2O$ (Mr 475.07): C, 50.56; H, 5.81; N, 17.69. Found: C, 50.58; H, 5.85; N, 17.63.

EXAMPLE 6

Preparation of N-[4-(3-(2,4-Diamino-1,6-dihydro-6-oxo-5-pyrimidinyl)propylamino)-2-chlorobenzoyl]-(L)-glutamic acid

(a) Preparation of Diethyl N-(4-nitro-2-chlorobenzoyl)-(L)-glutamate

A solution of 2-chloro-4-nitrobenzoic acid (10.0 g, 49.6 mmoles), (L)-glutamate diethyl ester hydrochloride (11.9 g, 49.6 mmoles), and 1-hydroxybenzotriazole (6.7 g, 49.6 mmoles) in dry dimethylformamide (2150 mL) was stirred under nitrogen while triethylamine (5.02 g, 6.92 mL, 49.6 mmoles) was added dropwise during 1 minute. After 15 minutes, 1,3-dicyclohexylcarbodiimide (11.3 g, 54.6 mmoles) was added in portions during 1 minute. The reaction mixture was filtered after 18 hours and the solids were rinsed with dichloromethane (2×50 mL). The filtrate was spin evaporated (high vacuum) to an amber residue that was dissolved in dichloromethane (300 mL). The organic phase was washed successively with saturated bicarbonate, 5% citric acid, and brine solution (1×300 mL each). The organic phase was then dried (MgSO$_4$), filtered, and poured onto a silica gel column (500 g, pre-wet with dichloromethane). The column was rinsed with dichloromethane (500 mL), followed by gradient elution of the product with 10% and 15% added ethyl acetate (8×250 mL fractions each). Like fractions were combined by spin evaporation and dried to give a white solid; yield, 9.8 g (51%); mp 95°–96° C.; $^1$H-NMR (DMSO-d$_6$) δ 1.17 and 1.21 (2t overlapped, 6H), 1.8–2.2 (m, 2H), 2.46 (t obscured by DMSO, 2H), 4.0–4.2 (2 q overlapped, 4H), 4.46 (m, 1H), 7.68 (d, $J_o=8$ Hz, 1H), 8.25 (dxd, $J_o=8$ Hz, $J_m=2$ Hz, 1H), 8.34 (d, $J_m$2 Hz, 1H), 9.14 (d, 1H); uv (MeOH) 260 nm max (9930), 236 min (6180), 205 max (25600); mass spec (CI) m/e 387 (100%), 341 (40), 184 (21).

Anal. Calcd. for $C_{16}H_{19}ClN_2O_7$ (Mr 386.78): C, 49.68; H, 4.95; N, 7.24; Cl, 9.17. Found: C, 49.71; H, 4.98; N, 7.23; Cl, 9.23.

(b) Preparation of Diethyl N-(4-amino-2-chlorobenzoyl)-(L)-glutamate

A solution of diethyl N-(4-nitro-2-chlorobenzoyl)-(L)-glutamate (4.00 g, 10.3 mmoles) in glacial acetic acid (200 mL) was stirred under nitrogen while zinc dust (10.0 g) was added in one portion. After 1.5 hours the reaction mixture was filtered and the solids were rinsed with glacial acetic acid (2×25 mL). The filtrate was spin evaporated (high vacuum) to a clear yellow residue that was washed with saturated bicarbonate solution (1×200 mL), dried (MgSO$_4$), filtered, spin evaporated, and dried to give a yellow oil (3.69 g, 100%) that shows a major spot in tlc (silica, 4:1 dichloromethane/ethyl acetate, R$_f$=0.3). The product was purified by the flash chromatography technique to give a light yellow wax; yield, 3.12 g (85%); $^1$H-NMR (DMSO-d$_6$) δ 1.16 and 1.18 (2 t overlapped, 6H), 1.8–2.1 (br m, 2H), 2.41 (t, 2H), 4.0–4.1 (2 q overlapped, 4H), 4.33 (m, 1H), 5.72 (br s, 2H), 6.48 (dxd, J$_o$=8 Hz, J$_m$=2 Hz, 1H), 6.57 (d, J$_m$=2 Hz, 1H), 7.16 (d, J$_o$=8 hz, 1H), 8.35 (d, 1H); uv (MeOH) 270 nm max (12600), 238 min (4500), 208 max (28800); mass spec (CI) m/e 357 (22%), 154 (100).

Anal. Calcd. for C$_{16}$H$_{21}$ClN$_2$O$_5$ (Mr 356.80): C, 53.86; H, 5.93; N, 7.85; Cl, 9.94. Found: C, 53.93; H, 5.95; N, 7.83; Cl, 10.03.

(c) Preparation of Diethyl N-[4-(3-(2-acetylamino-4-diacetylamino-1,6-dihydro-6-oxo-5-pyrimidinyl)propylamino-2-chlorobenzoyl]-(L)-glutamate Both diethyl-N-(4-amino-2-chlorobenzoyl-(L)-glutamate (2.84 g, 7.96 mmoles) and 3-(2-acetylamino-4-diacetylamino-1,6-dihydro-6-oxo-5-pyrimidinyl)propionaldehyde (2.70 g, 8.76 mmoles) were stirred in absolute ethanol (100 mL) under nitrogen while glacial acetic acid (6 mL) was added dropwise during 1 minute. After solution was achieved (0.5 hour), activated 3 Å molecular sieves (20 mL) were added and stirring was continued 3 hours. The reaction mixture was chilled (ice bath) and sodium cyanoborohydride (500 mg, 7.96 mmoles) added in one portion. After stirring cold 0.5 hour, the bath was removed and the reaction mixture allowed to warm to ambient temperature. The reaction mixture was filtered after 16 hours and the solids were rinsed with ethanol (100 mL). The filtrate was spin evaporated and dried to a cream foam that was dissolved in ethyl acetate (100 mL). The organic phase was washed with 1:1 brine/water (2×100 mL) and then poured onto a silica gel column (175 g, pre-wet with ethyl acetate). The column was rinsed with ethyl acetate (400 mL) and the product was eluted with 5% added methanol. Like fractions were combined by spin evaporation to give a white solid; yield, 2.28 g (44%); mp 63°–72° C. (eff); $^1$H-NMR (DMSO-d$_6$) δ 1.16 and 1.18 (2 t overlapped, 6H), 1.62 (m, 2H), 1.8–2.2 (br m, 2h), 2.12 (s, 3H), 2.23 (s, 6H), 2.26 (m, 2H), 2.42 (t, 2H), 2.99 (m, 2H), 3.9–4.2 (2 q overlapped, 4H), 4.34 (m, 1H), 6.29 (br t, 1H), 6.4–6.6 (m, 2H), 7.21 (d, J$_o$=8 hz, 1H), 8.35 (d, 1H), 11.9 (v br d, 2H); uv (MeOH) 289 nm max (26900), 257 min (13400), 207 max (44300); mass spec (FAB) m/e 649 (48%), 615 (22), 446 (100), 412 (46).

Anal. Calcd. for C$_{29}$H$_{37}$ClN$_6$O$_9$ (Mr 649.09): C, 53.66; H, 5.75; N, 12.95; Cl, 5.46. Found: C, 53.53; H, 5.80; N, 12.91; Cl, 5.42.

(d) Preparation of N-[4-(3-(2,4-Diamino-1,6-dihydro-6-oxo-5-pyrimidinyl)propylamino)-2-(chloro)benzoyl]-(L)-glutamic acid A solution of diethyl N-[4-(3-(2-acetylamino-4-diacetylamino-1,6-dihydro-6-oxo-5-pyrimidinyl)-propylamino-2-chlorobenzoyl]-(L)-glutamate (1.00 g, 1.54 mmoles) in 1.0N sodium hydroxide 25 mL) was stirred at 55° C. under nitrogen for 18 hours. The reaction mixture was chilled (ice bath) and adjusted to pH 2.5 by the gradual dropwise addition of 6N hydrochloric acid. After stirring cold 1 hour, the resulting precipitate was filtered, rinsed with cold pH 2.5 aqueous hydrochloric acid (2×25 mL), and dried to give a white solid; yield, 437 mg (61%); mp 150°–178° C. (eff); $^1$H-NMR (DMSO-d$_6$) δ 1.55 (m, 2H), 1.8–2.1 (m, 2H), 2.1–2.4 (m, 4H), 2.97 (m, 2H), 4.32 (m, 1H), 5.6–6.6 (v br s, 1H), 5.87 and 6.12 (2 br s, 4H), 6.50 and 6.52 (d and s overlapped, 2H), 7.23 (d, J$_o$=8 hz, 1H), 8.20 (d, 1H), 10.0–12.6 (v br s, 1H); uv (0.1N NaOH) 271 nm max (23000), 241 min (10000), 217 max (28000).

Anal. Calcd. for C$_{19}$H$_{23}$ClN$_6$O$_6$·1.3H$_2$O (Mr 490.30): C, 46.54; H, 5.26; N, 17.14; Cl, 7.23. Found: C, 46.66; H, 5.18; N, 17.04; Cl, 7.28.

Chemotherapeutic Data

A. Cell Culture Method for Evaluation of Compounds as Antitumor Agents Cells and Medium: MCF-7 reast adenocarcinoma, obtained from the American Type Culture Collection (ATCC) are grown in RPMI 1640 medium supplemented with 10 mM calcium leucovorin instead of folic acid as the folate source, 10% dialyzed fetal calf serum, penicilllin, streptomycin and sodium pyruvate (100 μg/ml).

Cytotoxicity Assay: Cells are seeded into 96 well plates using a Perkin Elmer Pro/pette. MCF-7 cells are seeded at 15,000 cells per well in 150 μl of medium. Prior to the addition of drugs, cultures were incubated for 24 hours at 37°. Compounds were added at 2x concentration in 150 μl of medium and each concentration was assayed in triplicate. Cultures were incubated for 72 hours in a 37° humidified incubator at 5% CO$_2$. Inhibition of cell growth was measured using the MTT dye reduction assay.

MTT Dye Reduction Assay: Cell dilutions for a standard curve were prepared from a 72 hour log-phase culture. Serial dilutions were seeded in triplicate in 96 well plates and incubated at 37 for 1 hour. MTT (3-(4,5-dimethylthiazol-2-yl)-2,5-diphenyltetrazoilum bromide) was dissolved in PBS at 5 mg/ml and sonicated for 30 seconds. Using the Perkin Elmer Pro/pette, 200 μl of medium was removed and 100 μl of MTT added to the wells of the standard curve and test plates. Suspension cultures were spun for 5 minutes at 1000 rpm before removing medium from the wells. Plates were incubated for 1 hour at 37° on a platform shaker. Following this incubation, 100 μl of medium was removed from the wells and 100 μl of DMSO added to each well. The plates were sonicated for approximately 10 seconds to solubilize the precipitated formazan dye. The absorbance of each well was measured using a Titertek Multiskan MC microtiter plate reader at 570 nm with a reference wavelength of 750 nm.

The compounds of Examples 2, 3, 4, 5 and 6 were found to be active in inhibiting the growth of MCF-7 -cells.

B. Cell Culture Cytotoxicity Test Data

The two routine indicator cell lines used are 1.) D98, a twice-cloned derivative of Detroit 98s from American Type Culture Collection (ATCC) strain CCL 18.1, from human sternal bone marrow and 2.) L, a cloned derivative from NCTC 929 (ATCC CCL1,) a $C_3H/An$ from mouse connective tissue. Inoculation densities for L and D98 cells are 1.0 and $1.5 \times 10^5$ cells, per cm$^2$, respectively. Control cells are grown in Eagle's MEM (Earle's salts, 10% horse serum, 100 units/ml potassium penicillin G and 100 µg/ml streptomycin) and should show at least two doublings during the test period. Test plates are seeded with similar quantities of cells and are grown in the same medium with test compounds added. Total "cell counts are made with an electronic cell counter after 70–76 hours of incubation with one medium change at 20–26 hours. Dose response curves are prepared by plotting percent of control vs. concentration of compound.

C. Reversal of Cytotoxic Activity

As mentioned previously, it may be necessary, in the treatment of prophylaxis of a neoplastic growth, to administer to the patient an antidote or rescue agent, such as calcium leucovorium or hypoxanthine.

D. Activity Against *Spiroplasma citri* Sensitivity Test

Frozen broth cultures are diluted to a predetermined titre of 100 color changing units for the test. Organisms are grown in Difco PPLO broth base with added serum, glucose, phenol red, ampicillin, thallium acetate and yeast extract. Incubation is at 32° C. Incubation with varying levels of the test compound in the above medium are performed in well plates and an amount of *Spiroplasma citri* cells is added that will produce a color change by a fixed time of growth. The lowest concentration of compound that fails to produce a color change or gives a two day delay in color change indicates minimum inhibitory concentration.

What I claim is:

1. A compound selected from the group consisting of:
   N-[4-(3-(2,4-diamino-1,6-dihydro-6-oxo-5-pyrimidinyl)propylamino)-2-fluorobenzoyl]-(L)-glutamic acid,
   N-[4-(3-(2,4-diamino-1,6-dihydro-6-oxo-5-pyrimidinyl)propylamino)-3-fluorobenzoyl]-(L)-glutamic acid,
   N-[4-(3-(2,4-diamino-1,1-dihydro-6-oxo-5-pyrimidinyl)propylamino)-3-methylbenzoyl]-(L)-glutamic acid,
   N-[4-(3-(2,4-diamino-1,6-dihydro-6-oxo-5-pyrimidinyl)propylamino)-3-(methoxy)benzoyl]-(L)-glutamic acid and
   N-[4-(3-(2,4-diamino-1,6-dihydro-6-oxo-5-pyrimidinyl)propylamino)-2-chlorobenzoyl]-(L)-glutamic acid,
   or a pharmaceutically acceptable salt thereof.

2. A compound according to claim 1 which is N-[4-(3-(2,4-diamino-1,6-dihydro-6-oxo-5-pyrimidinyl)-propylamino)-2-fluorobenzoyl]-(L)-glutamic acid or a pharmaceutically acceptable salt thereof.

3. A pharmaceutical formulation comprising a compound selected from:
   N-[4-(3-(2,4-diamino-1,6-dihydro-6-oxo-5-pyrimidinyl)propylamino)-2-fluorobenzoyl]-(L)-glutamic acid,
   N-[4-(3-(2,4-diamino-1,6-dihydro-6-oxo-5-pyrimidinyl)propylamino)-3-fluorobenzoyl]-(L)-glutamic acid,
   N-[4-(3-(2,4-diamino-1,6-dihydro-6-oxo-5-pyrimidinyl)propylamino)-3-methylbenzoyl]-(L)-glutamic acid,
   N-[4-(3-(2,4-diamino-1,6-dihydro-6-oxo-5-pyrimidinyl)propylamino)-3-(methoxy)benzoyl]-(L)-glutamic acid and
   N-[4-(3-(2,4-diamino-1,6-dihydro-6-oxo-5-pyrimidinyl)propylamino)-2-chlorobenzoyl]-(L)-glutamic acid,
   or a pharmaceutically acceptable salt thereof, and a pharmaceutically acceptable carrier therefor.

4. A pharmaceutical formulation according to claim 3 wherein said compound is N-[4-(3-(2,4-diamino-1,6-dihydro-6-oxo-5-pyrimidinyl)propylamino)-2-fluorobenzoyl]-(L)-glutamic acid or a pharmaceutically acceptable salt thereof.

* * * * *